United States Patent [19]

Nakanishi et al.

[11] Patent Number: 5,126,253
[45] Date of Patent: Jun. 30, 1992

[54] CELL LINES FOR USE IN THE PREPARATION OF HYBRIDOMA CELLS

[75] Inventors: Toshihiro Nakanishi, Osaka, Japan; Masashi Matsui, New York, N.Y.; Kenju Miura, Kyoto, Japan; Yoshiaki Fukuda, Osaka, Japan; Teruhisa Noguchi, Kanagawa, Japan

[73] Assignee: Suntory Limited, Osaka, Japan

[21] Appl. No.: 912,678

[22] Filed: Sep. 25, 1986

Related U.S. Application Data

[63] Continuation of Ser. No. 571,587, Jan. 17, 1984, abandoned.

[30] Foreign Application Priority Data

Jan. 20, 1983 [JP] Japan .................................. 58-7744
Jan. 20, 1983 [JP] Japan .................................. 58-7745

[51] Int. Cl.$^5$ ..................... C12P 21/08; C12N 15/00; C12N 5/00
[52] U.S. Cl. ................. 435/70.21; 435/172.2; 435/240.2; 435/240.26; 435/240.27; 435/948; 435/70.2
[58] Field of Search ............... 435/68, 172.2, 246, 435/241, 948, 70.2, 70.21; 935/93, 96, 99, 100, 102, 103, 104

[56] References Cited

U.S. PATENT DOCUMENTS

| | | | |
|---|---|---|---|
| 4,195,125 | 3/1980 | Wacker | 935/99 |
| 4,196,265 | 4/1980 | Koprowski et al. | 424/85 |
| 4,434,230 | 2/1984 | Ritts, Jr. | 435/948 |
| 4,693,975 | 9/1987 | Kozbor et al. | 435/948 |

FOREIGN PATENT DOCUMENTS

0093436 11/1983 European Pat. Off. ............. 935/93

OTHER PUBLICATIONS

Schumacher et al., "The Characterization of Four Monoclonal Antibodies Specific for Mouse IL-5 and Development of Mouse and Human IL-5 Enzyme-Linked Immunosorbent", Journal of Immunology, vol. 141, 1576-1581, No. 5, Sep. 1, 1988.
Harada et al., "Production of a Monoclonal Antibody Useful in the Molecular Characterization of Murine T—Cell-Replacing Factor/B-cell Growth Factor II", Proc. Natl. Acad. Sci. vol. 84, pp. 4581-4585, Jul. 1987.
Goding, Monoclonal Antibodies: Principles and Practice, Academic Press N.Y., (1983) p. 61.
Kahn et al., "Short-Lived Cytoplasmic Regulators of Gene Expression in Cell Cybrids", Nature 290 pp. 717-720 (1981).
Periman, "IgG Synthesis in Hybrid Cells from Antibody Producing Mouse Myeloma and an L Cell Substrain", Nature 228, pp. 1086-1087 (1970).
Imai et al., "Serological and Immunochemical Analysis of the Specificity of Xenoantiserum 8986 Elicited with Hybrids . . . ", Cancer Research 41 pp. 1026-1033 (1981).
Junker, "Regulation of Expression of Tyrosine Aminotransferase in Somatic Cell Hybrids between Rat Hepatoma Cells and Mouse Fibroblasts" Biochemical and Biophysical Research Communications 99(1), pp. 95-101 (1981).
Littlefield, "Selection of Hybrids from Matings of Fibroblasts in vitro and their Presumed Recombinants", Science 145, pp. 709-710 (1964).

(List continued on next page.)

*Primary Examiner*—John Doll
*Assistant Examiner*—Gail E. Poulos
*Attorney, Agent, or Firm*—Cushman, Darby & Cushman

[57] ABSTRACT

A novel cell line for use as a parent for hybridoma preparation is provided. This cell line is derived from tumor cells, in particular human tumor cells, other than those originating from bone marrow cells. A method for establishing this cell line is also provided. By fusing this cell line with cells producing useful physiologically active substances, such as B cells immunized with an antigen, a hybridoma capable of active growth can be prepared. This hybridoma can be cultivated for the production of useful physiologically active substances.

3 Claims, 2 Drawing Sheets

OTHER PUBLICATIONS

Olsson et al., "Human Hybridomas Producing Monoclonal Antibodies of Predefined Antigenic Specificity", Proceedings of the National Academy of Sciences 77(9), pp. 5429–5431 (1980).

Curry et al., "Serological Detectable Human Melanoma-Associated Antigens are not Genetically Linked to HLA-A and B Antigens", Journal of Immunology 122(6), pp. 2630–2632 (1979).

Malaya Bhattacharya, et al., "Monoclonal Antibodies Recognizing . . . ", *Cancer Research,* 42, 1650–1654, May 1982.

Susumu Hosoi, et al., "Detection of Human Osteosarcoma-associated Antigen(s) . . . ", *Cancer Research,* 42, 654–659, Feb. 1982.

F. James Primus, et al., "Immunological Heterogeneity of Carcinoembryonic Antigen: . . . ", *Cancer Research,* 43, 686–692, Feb. 1983.

Eva Engvall, et al., "Monoclonal Antibodies in Analysis of Oncoplacental Protein . . . ", *Cancer Research,* 42, 2028–2033, May 1982.

Arthur E. Frankel, et al., "Monoclonal Antibodies to a Human Prostate Antigen", *Cancer Research,* 42, 3714–3718, Sep. 1982.

Yuichi Iwaki, et al., "Monoclonal Antibody against $A_1$ Lewis d Antigen . . . ", *Cancer Research,* 42, 409–411, Feb. 1982.

G. Kohler and C. Milstein, "European Journal of Immunology", vol. 6, 511–519, Jul. 1976.

G. Kohler and C. Milstein, "Continuous Cultures of Fused Cells . . . ", *Nature, vol. 256, 495–497, Aug. 7, 1975.*

K. Imai et al., "Monoclonal Antibodies to Human Melanoma-Associated Antigens", *Transplantation Proceedings,* vol. XII, No. 3, 380–383, Sep. 1980.

Negoro et al.: "Several New Monoclonal Antibodies Directed . . . ", *Cancer Research* 42, 4259–4262, Oct. 1982.

Molecular Biology of the Gene, 4th Ed., James D. Watson et al., the Benjamin/Cummings Publishing Co., Inc., 1987, p. 844.

Nature, vol. 256, No. 5520, Aug. 28, 1975, pp. 751–753, Transformation of Human Cells in Culture by N-methyl-N'-nitro-N-nitrosoguanidine.

WELLS 1-6 : 2.5mm$\phi$
WELL 7 : 4.0mm$\phi$
DISTANCE BETWEEN WELL 7 AND EACH OF WELLS 1-6 : 4.0 mm
THICKNESS OF AGAROSE GEL : 1.5mm WELLS 1-4 : 2.5mm$\phi$
WELL 5 : 4.0mm$\phi$
DISTANCE BETWEEN WELL 5 AND EACH OF WELLS 1-4 : 4.0mm
THICKNESS OF AGAROSE GEL : 1.5 mm

CELL LINES FOR USE IN THE PREPARATION OF HYBRIDOMA CELLS

This is a continuation of application Ser. No. 571,587, filed Jan. 17, 1984, which was abandoned upon the filing hereof.

BACKGROUND OF THE INVENTION

1. Field of the Invention

The present invention relates to novel cell lines for use as a parent in hybridoma preparation which cell lines are established from human tumor cells other than those derived from bone marrow cells. The invention also relates to a method for establishing these novel cell lines, as well as novel hybridomas prepared by fusing cells of these parent cell lines with cells of another parent (hereunder referred to as partner) from human and animal cells. The invention further relates to a process for producing useful substance such as antibodies or lymphokines by culturing the novel hybridomas.

2. Description of the Prior Art

In the fields of immunology, biology, medical science and pharmacology, intensive efforts are being made to use as diagnostic agents or therapeutic agents the homogeneous and very highly specific antibodies (monoclonal antibodies) produced from hybridoma cells that can be grown in vitro and have the ability to produce antibodies to specific antigens. The possibility of preparing the hybridomas and using them in the production of biological substances in vitro was first demonstrated in 1975 by Ceaser Milstein and his co-workers at Cambridge University (Milstein C. et al, "Nature", 256, 495). They prepared a mutant cell line (P3-X63-Ag8) from a mouse myeloma strain (P3K) endowed by Leo Sacks of Salk Institute. The mutant cells were then fused with mouse spleen cells immunized with sheep red blood cells (SRBC). The resulting hybridoma was found to be capable of growing in vitro and producing monoclonal antibodies (MoAb) to SRBC. One great advantage of using hybridomas is that it provides a tool for mass production of biologically active substances by fusing tumor cells having high proliferative ability with those which can produce such biologically active substances but which usually have little or no proliferative ability in vitro.

Following the report by Milstein et al., many researchers made studies on hybridomas producing MoAb to specific antigens. In all of these studies, parent cells for use in the preparation of hybridomas were tumor cells derived from bone marrow cells such as myeloma cells and tumor cells from B cells. The genetic properties of tumor cells such as myeloma cells that are necessary for preparing hybridomas and the theoretical aspect of the hybridoma preparation are described hereunder in detail.

The first requirement for the preparation of a hybridoma from two or more kinds of parent cells is to use a system in which only the hybridized cells survive, the survival of the parents being prevented. Therefore, in most of the attempts at preparing hybridomas, tumor cells that can grow vigorously in vitro are such mutant cells as are deficient in either hypoxanthine-guanine phosphoribosyl transferase (HGPRT) or thymidine kinase (TK). The genetic and biochemical behavior of both mutants is essentially the same, so the following description will be made based on the more common HGPRT-deficient cells. As is well known, HGPRT is one of the enzymes that is responsible in all cells for DNA synthesis by a salvage circuit in the route of the DNA synthesis. More specifically, if the DNA synthesis in the de novo circuit requiring components of purine or pyrimidine as substrates for the enzymatic reaction is suppressed by a certain inhibitor (e.g. aminopterin), the HGPRT actuates the salvage circuit as a rescue pathway and enables the continued DNA synthesis to keep the cells alive. Therefore, no HGPRT-deficient cells can survive in a medium containing hypoxanthine, aminopterin and thymidine (HAT medium) due to the presence of aminopterin which is an inhibitor against the de novo circuit. The partner cells for the preparation of a hybridoma, for example spleen cells (B cells), are capable of synthesizing DNA through both the de nove and salvage circuits. Therefore, the hybridoma produced by fusing the spleen cells with the HGPRT-deficient parent cells survives the inhibition of the de novo circuit by aminopterin in the HAT medium and effectively makes use of hypoxanthine to synthesize DNA through the salvage circuit originating from the spleen cells. In other words, the hybridoma posseses both the ability of the parent myeloma cells to grow vigorously in vitro and the ability to synthesize DNA by the salvage circuit originated from the spleen cells even under the inhibition of the de novo circuit in the presense of aminopterine in the HAT medium. Furthermore, the hybridoma has the genetic information from the spleen cells to produce immunoglobulins (antibodies) to specific antigens, so it is capable of growing in the HAT medium to produce immunoglobulins.

The HGPRT-deficient strain as a parent for the hybridoma preparation is usually selected as a cell line that is generated by a suitable mutation technique and which is resistant to 8-azaguanine and is unable to grow in the HAT medium. Conventionally, this parent consists of bone marrow derived tumor cells such as myeloma cells or B cell lymphoma. However, most of the tumor cells that can be cloned for use in the hybridoma preparation originate from mice or rats and human myeloma cells are seldom used. The reasons are: 1) clones that can be subjected to selection in the HAT medium (hereunder sometimes referred to as HAT selection) are difficult to prepare from human myeloma cells; 2) human myeloma cells do not have the high proliferative ability that is required for a parent, so a hybridoma prepared by fusing them with partner cells has only a limited ability to grow, and furthermore, it is not stable enough to produce a large amount of the desired substance such as immunoglobulins. Therefore, it has ben impossible in the art to prepare human-human hybridomas that have sufficient growing ability and produce useful substances. Researchers are unable to produce human immunoglobulins in quantity from cultured cells and instead they have to use immunoglobulins originating from animal-animal hybridoma cells. However, the immunoglobulins produced from animal-animal hybridomas are proteins which are foreign to humans, so their antigenicity prevents their extensive use in humans. Therefore, it is strongly desired to produce immunoglobulins from human-human hybridomas. But, as already mentioned, the mass cultivation of hybridomas from human myeloma cells involves great difficulty because of their instability.

Myeloma cells produce large quantities of immunoglobulins called myeloma proteins. However, it is not known whether the thus produced immunoglobins are antibodies to any specific antigens, and it is almost impossible to select myeloma cells producing an antibody to a specific antigen. Scientists have concluded that the presence of myeloma proteins complicates the screening of hybridomas or the purification of antibodies, so myeloma cells that produce myeloma proteins are being replaced by those which do not produce myeloma proteins. In other words, the growing ability in vitro is now regarded as a more important factor for the myeloma cells as a parent for the hybridoma preparation.

Under these circumstances, it is desired to obtain human cells as a parent cell line for hybridoma preparation that will grow vigorously and can be subjected to HAT selection after fusion with partner cells, as well as human hybridomas that remain sufficiently stable in vitro to produce large quantities of the desired substances such as immunoglobulins. It has been generally understood that the parent cells to be fused with partner cells for hybridoma preparation should be selected from among cancer cells derived from myeloma and B cells [including cells transformed by Epstein Barr virus (EBV)]. However, as mentioned before, these parent cells have various defects that prevent their extensive use in clinical applications.

SUMMARY OF THE INVENTION

Therefore, one object of the present invention is to establish an entirely new type of consistent human cell line to be fused with partner cells to prepare hybridomas, such cell line being free from the defects of the conventional cell line that has previously been used as a parent. This is based on the understanding of the presnet inventors that any cell that is capable of growing vigorously in vitro can be used as a parent to be fused with partner cells in hybridoma preparation.

More specifically, one object of the present invention is to establish a new type of human cell line from a cell mutant produced either by natural or induced mutation of cancer cells originating from cells other than myeloma cells or B cells, such as tumor cells typified by epidermal cancer (melanoma), hepatoma, gastric cancer, intestinal cancer, lung cancer and breast cancer cells, preferably human melanoma, hepatoma and lung cancer cells. Specific examples of the mutant are genetically deficient cells that are unable to produce some of the enzymes responsible for the DNA synthesis.

Another object of the present invention is to establish a parent cell line that is more proliferative in vitro than the conventional cell lines from bone marrow-derived tumor cells (myeloma cells) and which may be fused with antibody-producing cells (B cells) to provide a hybridoma that is as proliferative as the parent cell and which yet remains stable enough to produce immunoglobulins.

Still another object of the present invention is to provide a hybridoma from said parent cell line that remains sufficiently stable in vitro to produce a useful substance such as an antibody. More specifically, the present invention intends to prepare a specific antibody producing hybridoma by fusing said parent cell line, in particular, of a human tumor cell line with B cells from animals other than humans that are sensitized with a specific antigen.

A further object of the present invention is to prepare a specific antibody producing human-human hybridoma by fusing said parent cell line with B cells from the peripheral blood, tonsil, lymph node or spleen cells of humans sensitizd with a particular antigen.

A still further object of the present invention is to prepare a human-human hybridoma that produces human immunoglobulins and which can be administered to humans without causing the problem of undesired antigenicity.

Yet another object of the present invention is to prepare a T-cell hybridoma by fusing said parent cell line with human T cells capable of producing gamma-interferon or lymphokines.

A further object of the present invention is to provide a process for producing a useful substance such as an antibody, interferon or lymphokines either directly from said hybridoma or from a culture of said hybridoma.

DETAILED DESCRIPTION OF THE INVENTION

Figure 1:
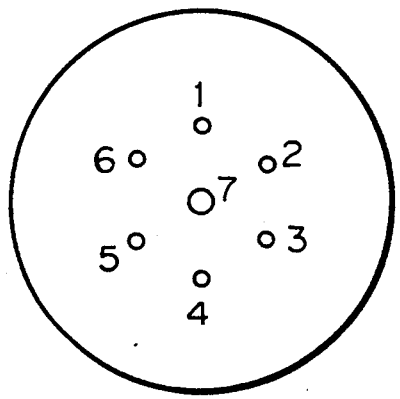
FIGS. 1 and 2 are each a plan view showing schematically the method of the Ouchterlony test conducted in Experiment 1.

The method of preparing the novel tumor cell line for hybridoma preparation according to the present invention, the method of preparing a hybridoma using this cell line as a parent, and the process for producing a useful biological substance from this hybridoma are described hereinafter. The parent cell line for hybridoma preparation according to the present invention can be obtained either by natural mutation or induced mutation of tumor cells other than those derived from bone marrow cells, in particular, of human tumor cells such as human melanoma cells, human lung cancer cells and human hepatoma cells. The hybridoma according to the present invention can be prepared by fusing this novel cell line with another parent i.e. partner derived from, for example, the B cells of animals including humans immunized with a particular antigen. For the sake of simplicity, the present invention is hereunder described with particular reference being made to the embodiment of producing a monoclonal antibody (MoAb) from the culture of a hybridoma prepared by fusing human tumor cells with mouse spleen cells. It should be understood however that the present invention is by no means limited to this particular embodiment.

The process of preparing the human tumor cells as a parent for hybridoma preparation starts with the isolation of a clone deficient in an enzyme (HGPRT) involved in DNA synthesis in the salvage circuit in order to permit the subsequent HAT selection of hybridomas. This step can be carried out by one of the following two methods. In one method, a suitable concentration of 8-azaguanine is directly added to a culture medium so as to obtain an 8-azaguanine resistant strain. In the other method, cancer cells are treated with either UV irradiation or a mutation inducer depending upon the specific type of the cancer cells, and the so treated cells are subsequently transferred into an 8-azaguanine containing medium. The UV irradiation is performed by exposing the cells to a UV lamp (GL-15) 30 cm above for a period of 15 seconds to 10 minutes. A suitable mutation inducer is ethylmethane sulfonate (EMS) or N-methyl-N'-nitro-N-nitrosoguanidine (MNNG) and is used in an amount of 0.05-10 μg/ml. After cultivating the cells in the presence of the mutation inducer for a period of several hours to 3 days, the culture is thoroughly washed with a serum-free medium and transferred to an 8-azaguanine containing medium. Whichever method is used, the first step of the process ends with the appearance of one or more 8-azaguanine resistant strains.

The second step consists of checking to see if the cells of the 8-azaguanine resistant strain permit the subsequent HAT selection. Cells of the 8-azaquanine resistant strains are cultivated in a suitable medium, which is then removed by centrifugation. The cells are then washed with HAT medium twice and transferred to a fresh HAT medium ($10^5$ cells/ml). After a 5-day incubation, the cells are stained with trypane blue. If almost all of the cells are found to be dead, cells of the same 8-azaguanine resistant strain ($10^5$ cells/ml) are plated on Costar No. 3596 (a micro-plate with 96 wells) after $10^5$ feeder cells (e.g. spleen cells) have been plated in each well. Before the plating, the 8-azaguanine resistant cells are diluted to such a concentration that will ensure that no more than one cell is present in each well (0.1 cell/well by probability). The plated cells are incubated for about one week. Clones are allowed to increase in cell population and when they reach about $10^5$ cells/ml, they are again fed with an HAT medium and are then left until all of them die. The above procedure is preferably repeated at least twice. The second step ends with the confirmation of the complete death of 8-azaguanine resistant cells in the HAT medium. It is required that 8-azaguanine be always added in the HAT medium until the desired cell line is established.

In the above procedures, 8-azaguanine may be replaced by BudR, where clones deficient in TK and again sensitive to HAT medium may be obtained. After the establishment of the desired cell line, it is kept in a medium containing 8-azaguanine, if appropriate. The medium for culturing the established cell line may be the same as what was used before the mutation of the human tumor cells. Moreover, the established cell line can be used as a parent for the hybridoma preparatin without requiring a special medium composition. The established cell line can be effectively stored by a conventional method by suspending in a medium containing 10% FCS (fetal calf serum) and 10% DMSO (dimethyl sulfoxide), which is then kept in either liquid nitrogen or a freezer of ca. −80° C or below.

The established cell line of the present invention is useful as a parent for the preparation of a hybridoma. If the cell line originates from human tumor cells, it will be suitable as a parent for the preparation of a human-human hybridoma. The other parent (partner cells) may be B cells from the peripheral blood, tonsil, lymph node and spleen of humans immunized with a particular antigen. One great advantage of the human-human hybridoma is that it is expected to produce immunoglobulins which are human proteins and hence can be administered to humans without causing the problem of undesired antigenicity. More importantly, the present invention is believed to enable the preparation of hybridomas not only from human B cells but also from human T cells. Thus, the parent cell line according to the present invention may be fused with a partner which is a human T cell capable of producing gamma-interferon or lymphokines. The resulting T-cell hybridoma is expected to have the ability to produce the gamma-interferon and lymphokines. Therefore, the cell lines of the present invention find a wide range of applications and can be used to prepare various types of hybridomas.

The process for preparing a hybridoma using the established cell line as a parent proceeds as follows. The medium to be used may be any one of the common mediums such as Eagle MEM, Dulbecco's improved MEM and RPMI 1640 that contain 10% CS (calf serum), 5% FCS +5% CS or 10% FCS. For the usual maintenance of the parent cells, any one of these media may be used, but for the specific purpose of hybridoma preparation, 10% FCS is preferred. In the first step, parent cells, i.e. human cancer cells and partner cells, i.e. spleen cells, are fused in a ratio of 1:5, with HVJ (hemagglutinating virus of Japan, also known as Sendai virus) or polyethylene glycol (PEG) used as a mediator. A 30-50% solution of PEG 1000 is preferred. The fused cells can be subjected to HAT selection by the procedure that is described hereinbefore. The screening of the resulting hybridoma cells is effected mainly by checking the supernatant of the culture for the appearance of immunoglobulins, to pick up hybridoma clones producing immunoglobulins by the SPA-bind-SRBC method (SPA: Staphylococcus aureus protein A; see "Procedures of Immunological Experiments VII", p. 2375) or ELISA method (Dynatech method). The clones are allowed to increase gradually in cell population and when they reach $10^5$ cells/ml, they are subjected to subcloning. In order to ensure that all of the hybridoma cells are monoclonal, they are plated on a microplate with 96 wells in each of which about $10^5$ normal spleen cells have been plated as a feeder layer. The hybridoma cells should be diluted to such a concentration that ensures that no more than one hybridoma cell is present in each well (average number of 0.1 cell/well by probability). After an incubation for about one week, the resulting clones are checked for their ability to produce a specific antibody. The above procedure is repeated until monoclonal hybridoma cells are obtained.

The immunoglobulins produced by the hybridoma can be easily checked for their classes and subclasses by the Ouchterlony technique using an agarose gel. Antibodies to the immunoglobulins that are expected to be produced by the hybridoma are caused to react with the culture supernatant on an agarose plate, and a precipitation line appearing 24 hours later is observed. For details of the Ouchterlony method, see Experiment 1.

As will be apparent from the foregoing description, the present invention denies the conclusion of Milstein et al. that a parent cell line for the hybridoma preparation must be that of tumor cells such as myeloma or B cell lymphoma originated from bone marrow cells. In other words, the present inventors have demonstrated that any tumor cells that are capable of growing in vitro can be used for the establishment of parent cell lines for hybridoma preparation. The established human tumor cell line of the present invention can be cultured more simply than the conventional myeloma cell line and yet it is more stable and proliferative than the latter. By using this cell line as a parent, a human-mouse hybridoma can be prepared in the present invention. According to the present invention, not only a hybridoma producing a monoclonal antibody but hybridomas that produce lymphokines having useful physiological activities will also be prepared.

The method of preparing the parent cell line of the present invention for hybridoma preparation, the process for preparing a hybridoma from said parent cell line, as well as the process for producing an antibody from the resulting hybridoma and the method for its identification are hereunder described by working examples and experimental data.

EXAMPLE 1

Preparing from Human Tumor Cell Colo 38 a Parent Cell Line for Hybridoma Preparation (Method A)

In the following working examples, all cultivations were conducted in an atmosphere of 5% $CO_2$+95% air at a relative humidity (r.h.) of ca. 100% and 37° C.

Human malignant melanoma cells (Colo 38SBM 321) were cultured for 2 or 3 days until they reached a log phase. To the cells, a mutation inducer MNNG (N-methyl-N'-nitro-N-nitrosoguanidine of Sigma Chemical Co.) was added to give a final concentration of 0.05–10 μg/ml. After 36 hours of incubation at an MNNG concentration of 5 μg/ml, about 20% of the melanoma cells were found to be dead. The culture was freed of MNNG by washing with serum-free RPMI 1640 (product of Nissui Seiyaku Co., Ltd.) under three centrifugations. A total of 10 ml of the so treated cells ($2 \times 10^5$ cells/ml) were added to a medium containing 8-azaguanine at a final concentration of 1–50 μg/ml. The culture was continued for at least one week at respective 8-azaguanine concentrations that assured at least 99% of the cells would die within one week in 20 μg/ml of 8-azaguanine. At this 8-azaguanine concentration, the culture was continued for at least two weeks from commencement with daily observation of cell growth. About two weeks later, a rapid growth of the cells occurred. Therefore, the cells were collected by centrifugation and added to a medium containing 8-azaguanine at a final concentration of 50 μg/ml (the number of cells added was the same as those used in the first treatment with 8-azaguanine: $2 \times 10^5$ cells/ml). The cells that survived a 2-week incubation in the medium were selected as 8-azaguanine resistant strains.

Cells of the 8-azaguanine resistant strains were washed with a serum-free medium by three centrifugations and transferred into 10 ml of an HAT medium. The medium consisted of RPMI 1640 medium supplemented with 10% FCS (product of CSL Co., Australia) to which were added hypoxanthine, aminopterin and thymidine in respective final concentrations of $10^{-4}$ M, $4 \times 10^{-7}$ M and $1.6 \times 10^5$ M. The concentration of the cells in the HAT medium was $10^5$ cells per ml. On the 5th day of the incubation, the cells were checked for their survival by staining with trypane blue. If all of the cells were found to be dead in the HAT medium, another portion of the 8-azaguanine resistant cells of the same strain was plated in 96 wells at a probability of 0.1 cells/well together with spleen cells which had been plated in each well as a feeder layer at a concentration of $10^5$ cells/well. After incubation for about one week, six clones formed among 96 wells. By continuing the incubation for another one or two weeks, the number of cells in each clone increased to about $10^5$/ml. Thereafter, all clones were subjected to HAT selection. The cells in each clone died within 5 days. One of the six clones was again plated in 96 wells in the same manner and subcloned to obtain 8 clones. They were also allowed to increase in number and were subjected to HAT selection to confirm that all cells had died in the HAT medium.

The so obtained human malignant melanoma cells that were resistant to 8-azaguanine and sensitive to HAT selection were named cell lines of ME 1 series. They were stored with a medium [10% FCS, 10% DMSO (dimethyl sulfoxide) and 80% ordinary medium] in liquid nitrogen or within a freezer at ca. $-80°$ C.

EXAMPLE 2

Preparing from Human Tumor Cell Colo 38 a Parent Cell Line for Hybridoma Preparation (Method B)

Method B differed from method A in that a mutation was induced by UV irradiation rather than by a chemical inducer. The human malignant melanoma cells in a log phase were put in a Petri dish (10 cmφ) at a concentration of $2 \times 10^5$ cells/ml (total 10 ml). After irradiation with a UV lamp (GL-15 of Matsushita Electric Industrial Co., Ltd.) positioned 30 cm above, 8-azaguanine was added to the cells at a final concentration of 20 μg/ml. Within about one week, at least 99.5% of the cells died. The incubation was continued for about two more weeks under the same condition with daily observations. About three weeks after the first addition of 8-azaguanine, the number of the cells increased rapidly to form a uniform suspension of cells. They were collected by centrifuge and added to a medium at a concentration of $2 \times 10^5$ cells/ml in the presence of 8-azaguanine at a final concentration of 50 μg/ml. The cells that survived an incubation for two more weeks were selected as 8-azaguanine resistant cells.

These cells were subsequently subjected to HAT selection as in Example 1, and three cell lines of ME 1 series were obtained. The probability for the appearance of 8-azaguanine resistant cells was about one fifth of the value achieved in Example 1. However, the probability at which 8-azaguanine cells were sensitive to HAT selection was the same for both Examples.

EXAMPLE 3

Preparing from Human Tumor Cell Colo 38 a Parent Cell Line for Hybridoma Preparation (Method C)

Method C differs from Methods A and B in that 8azaguanine is directly added to a culture medium of human tumor cells. A culture (10 ml) containing $2 \times 10^5$/ml of human malignant melanoma cells (Colo 38) in a log phase was incubated for 5 days in the presence of 8-azaguanine at a concentration of 5 μg/ml. Thereafter, the amount of 8azaguanine was increased to give a final concentration of 20 μg/ml. Within 10 days of the inubation, almost all cells died. But the incubation was continued for about 20 more days under the same condition. The probability of achieving cell growth was low but a rapid increase in the number of cells occurred in one of the 18 flasks tested. A portion of the increased cells was cultured for two more weeks in the presence of 8-azaguanine at a final concentration of 50 μg/ml. The cells that were capable of normal growth in this condition were selected as 8-azaguanine resistant cells.

These cells were subsequently subjected to HAT selection as in Example 1 and six cell lines of ME 1 series were obtained.

In Examples 1 to 3, a total of 17 cell lines of ME 1 series were prepared from human malignant melanoma cells (Colo 38) by three different methods. The cell lines were identified as SUN N-21-1 to SUN N-21-17.

EXAMPLE 4

Preparing from Human Tumor Cells (M 21) a Parent Cell Line for Hybridoma Preparation This example shows that a parent cell line for hybridoma preparation can also be prepared from human tumor cells other than Colo 38. The method used in Example 4 was substantially the same as in Example 1.

Human melanoma cells (M 21) were cultured for 60 hours until they reached a log phase. A mutation inducer MNNG was added to the cells at a final concentration of 5 µg/ml. After 36 hours of incubation, during which about 35% of the melanoma cells were found to be dead, the culture was freed of MNNG by washing with serum-free RPMI 1640 under three centrifugations. $2 \times 10^5$ viable cells per ml (10 ml) were incubated in a medium containing 8-azaguanine at a final concentration of 20 µg/ml. Within a week, at least 99.5% of the cells died, but the incubation was continued for two more weeks under the same condition.

The culture was checked once a day for any cell growth under a microscope. About 20 days later, a gradual increase in the number of cells occurred, and within 5 more days, a rapid cell growth occurred. The growing cells were collected by centrifuge and $2 \times 10^5$ cells/ml were suspended in a medium (10 ml) containing 8-azaguanine at a final concentration of 50 µg/ml. The incubation was continued for about 2 weeks and those cells which had increased in number were selected as 8-azaguanine resistant cells.

These cells were subjected to HAT selection and repeated subcloning as in Example 1. As a result, six parent cell lines for hybridoma preparation that were resistant to 8-azaguanine and which died in the HAT medium could be obtained from human melanoma cells M-21. These six cell lines were identified as SUN N-22-1 to SUN N-22-6 of ME 2 series.

EXAMPLE 5

Preparing from Human Hepatoma Cells a Parent Cell Line for Hybridoma Preparation (Method D)

Human hepatoma cells HC C-4 were cultured in RPMI 1640 for 24 hours. To the culture, a mutation inducer EMS (ethyl-methane sulfonate of Sigma Chemical Co.) was added to give a final concentration of 1 mM. By a 3-hour incubation, a mutation was induced in the human hepatoma cells HC C-4. The cells were then washed three times with a serum-free RPMI 1640 medium, cultured in whole (serumcontaining) RPMI 1640 medium for a period ranging from 48 to 72 hurs, and subsequently cultured for 3-4 weeks in an RPMI 1640 medium containing 2.0 µg/ml of 8-azaguanine. About 3 weeks later, a rapid increase occurred in the number of cells and uniform clones of adherent cells formed. The culture was incubated for two more weeks in an RPMI 1640 medium containing 10 µg/ml of 8-azaguanine. The growing cells were selected as 8-azaguanine resistant cells.

These cells were subsequently checked for their sensitivity to HAT selection as in Example 1. As a result, 8 clones of HGPRT-deficient cell lines as a parent for hybridoma preparation could be obtained from human hepatoma cells. These clones were identified as SUN N-31-1 to SUN N-31-8.

EXAMPLE 6

Preparing from Human Hepatoma Cells a Parent Cell Line for Hybridoma Preparation (Method E)

As in Example 5, a culture of human hepatoma cells HC C-4 was treated with a mutation inducer EMS. The culture was then freed of EMS by washing with a serum-free RPMI 1640 medium. The culture was incubated for 3-4 weeks in a medium containing 2.0 µg/ml of BudR (bromodeoxyuridine of Sigma Chemical Co.). The growing cells were transferred into a medium containing 10 µg/ml of BudR, where they were incubated for about 2 weeks. The cells that achieved growth in this incubation was selected as BudR-resistant cells.

They were subsequently checked for their sensitivity to HAT selection as in Example 1. As a result, six clones of TK-deficient cell lines as a parent for hybridoma preparation could be obtained from human hepatoma cells. These clones were identified as SUN N-32-1 to SUN N-32-6.

EXAMPLE 7

Preparing from Human Lung Carcinoma Cells a Parent Cell Line for Hybridoma Preparation Human lung carcinoma cells A-549 were cultured in RPMI 1640 medium for 24 hours. To the culture, a mutation inducer EMS was added to give a final concentration of 1 mM. By a 3-hour incubation, a mutation was induced in the human lung carcinoma cells A-549. The cells were then washed three times with a serum-free RPMI 1640 medium, cultured in a whole RPMI 1640 medium for a period ranging from 48 to 72 hours and subsequently cultured for 3-4 weeks in the RPMI 1640 medium containing 2.0 µg/ml of BudR. About 3 weeks later, a rapid increase occurred in the number of cells and a uniform layer of adherent cells formed. The culture was incubated for two more weeks in the RPMI 1640 medium containing 10 µg/ml of BudR. The cells that achieved growth were selected as BudR resistant cells.

These cells were subsequently checked for their sensitivity to HAT selection as in Example 1. As a result, five clones of TK-deficient cell lines as a parent for hybridoma preparation could be obtained from the human lung cancer cells. These clones were identified as SUN N-33-1 to SUN N-33-5.

The parent cell lines that were established in Examples 1 to 7 can fuse with B cells such as spleen cells to form hybridomas which produce immunoglobulins in the culture, as is demonstrated by the following Example.

EXAMPLE 8

Preparation of Hybridoma by Fusing ME 1 of Example 1 with Mouse Spleen Cells Immunized with Human Lung Carcinoma Cells (A-549) and Confirmation of the Secretion of Monoclonal Antibody from the Hybridoma A culture of 107 cells of SUN N-21-2 (parent cells) was fused with $5 \times 10^7$ spleen cells (partner cells) of a female BALB/c mouse (4 weeks old) that had been inoculated once a week with human lung carcinoma (A-549) for 4 weeks at a dose of 107 cells per time. Polyethylene glycol (PEG 1000 of Wako Pure Chemical Industries, Ltd.) was used as a fusion mediator at a concentration of 40%. The fusion procedure was as follows. The parent cells and the partner cells were mixed and centrifuged in a centrifugal tube and the supernatant was discarded. About 0.5 ml of PEG 1000 that had been diluted to 40% with RPMI 1640 was added to the packed cells. The mixture was left to stand for 3 minutes and centrifuged at 500 rpm for 3 minutes. Thereafter, about 5 ml of a medium was slowly added, and the mixture was centrifuged and the supernatant was discarded. All the cells were slowly transferred into a T-75 flask (Falcon No. 3024), and the medium was further added to make a total volume of about 40 ml. Following a cultivation over-night, the culture including all the cells was transferred into a centrifugal tube and the supernatant was discarded after centrifugation. An HAT medium (40 ml) was added to the packed cells and stirred thoroughly. The mixture was distributed among 96 wells in a microplate in an amount of about 100 μl per well. The same procedure was repeated to fill the wells of four microplates with a mixture of cells and HAT medium. Following a one-week incubation, colonies formed in about 10% of the wells. These colonies had a tendency to spread more flatly than the colony of the parent cells. Starting in the first week of the incubation, a drop (ca. 25–30 μl) of HT medium (the same as HAT medium except that aminopterin is not included) was added to each well. When a reasonable growth of hybridoma had taken place (ca. 10–14 days later), the supernatant of the culture was checked for the appearance of a monoclonal antibody to the human lung carcinoma (A-549) by the Protein A-bind-SRBC method. Four of the 45 clones formed were found to produce a monoclonal antibody to A-549. One of these four clones was subcloned as in Example 1. Four subclones grew and they all produced a monoclonal antibody to A-549.

These hybridoma cells could be stored by known methods such as by suspending in a medium (10% FCS, 10% DMSO and 80% ordinary medium) and stored in liquid nitrogen or in a freezer at ca. −80° C.

EXPERIMENT 1

Determination by Ouchterlony Method of Class and Subclass of the Immunoglobulins Produced by the Hybridoma Prepared in Example 8

A 15% agarose solution (5 ml, with 0.01% NaN₃) was put into four Petri dishes (I.D.=52 mm) and left to stand for about 30 minutes until the agarose solidified. Wells were punched in the agarose gel in each dish as shown in FIG. 1. In the peripheral wells, 5 μl each of the antibodies listed in Table 1 was added, whereas the center wells in the respective agarose gels were filled with 15 μl each of 10-fold concentrate of cultured medium containing four monoclonal antibodies (LAC 1, 2, 3 and 4) produced by the hybridoma prepared in Example 8. The gels were left to stand for 24 hours, and the class of each monoclonal antibody was determined by the formation of the precipitation line.

TABLE 1

| No. | Antibody | Origin |
| --- | --- | --- |
| 1 | anti-human IgM (Hoechst AG) | Rabbit |
| 2 | anti-human IgG (Hoechst AG) | Rabbit |
| 3 | anti-mouse IgG (Capel Co.) | Rabbit |
| 4 | anti-mouse IgM (Hoechst AG) | Sheep |
| 5 | anti-human Ig(G + A + M) (Hoechst AG) | Sheep |
| 6 | anti-human IgA (Hoechst AG) | Rabbit |

The four monoclonal antibodies tested were found to be mouse IgG because all the precipitation lines were formed between well 3 and the central well 7.

Figure 2:
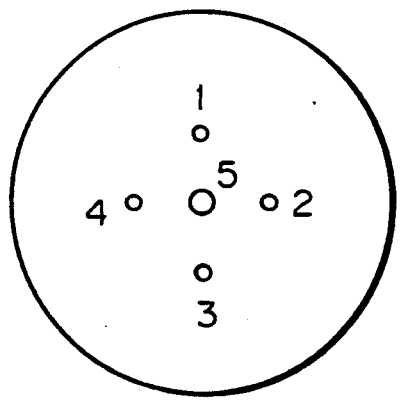

The subclass of IgG was determined by the same procedure. As shown in FIG. 2, five wells were punched in the agarose gel in each of the four Petri dishes. The four peripheral wells were filled with 5 μl each of the antibodies of the subclasses listed in Table 2, and the center wells in the respective agarose gels were filled with 15 μl each of the monoclonal antibodies (LAC 1–4). The Petri dishes were left to stand for 24 hours at room temperature.

TABLE 2

| No. | Antibody | Origin |
| --- | --- | --- |
| 1 | anti-mouse IgG1 (Miles Labs., Inc.) | Rabbit |
| 2 | anti-mouse IgG2a (Miles Labs., Inc.) | Rabbit |
| 3 | anti-mouse IgG2b (Miles Labs., Inc.) | Rabbit |
| 4 | anti-mouse IgG3 (Miles Labs., Inc.) | Rabbit |

The four monoclonal antibodies tested were found to be IgG2a because their precipitation lines were formed between wells 2 and 5.

The amounts of the monoclonal antibodies produced by the hybridoma of Example 8 were about 30 μg/ml which was almost the same as those of the monoclonal antibodies produced by the hybridomas prepared by using mouse myeloma cells as a parent. The unity of the antibodies produced by the hybridoma of Example 8 was further confirmed by gel electrophoresis.

The above results show that the human parent cell lines according to the present invention (e.g. SUN N-21-1 of ME 1 series) as fused with B cells produce immunoglobulins expressing the genetic information given from the B cells.

The human myeloma cells that have been attempted to be used as a parent for hybridoma preparation have various defects such as difficulty in cultivation, low growth rate and instability. However, as shown below, the cell line of the present invention is capable of consistent growth which 25 is the inherent nature of cancer cells.

EXPERIMENT 2

Growth Profiles of Cancer Cells and ME 1 Cell Line of the Present Invention

A culture (10 ml) of 2×10⁵ human melanoma cells (Colo 38) per ml was incubated in RPMI 1640+10% FCS. A culture (10 ml) of 2×10⁵ cells/ml of SUN N-21-1 of ME 1 series derived from Colo 38 was also incubated in RPMI 1640 ±10% FCS. Another culture (10 ml) of an equal number of SUN N-21-1 cells was incubated in RPMI 1640 +10% FCS containing 8-azaguanine at a final concentration of 20 μg/ml. Samples were taken and the number of viable cells in each culture was counted. The results are depicted in FIG. 3 from which one can see that the growth profile of SUN N-21-1 is similar to that of human melanoma Colo 38 and experiences little change even in the presence of 8azaguanine.

Figure 3:
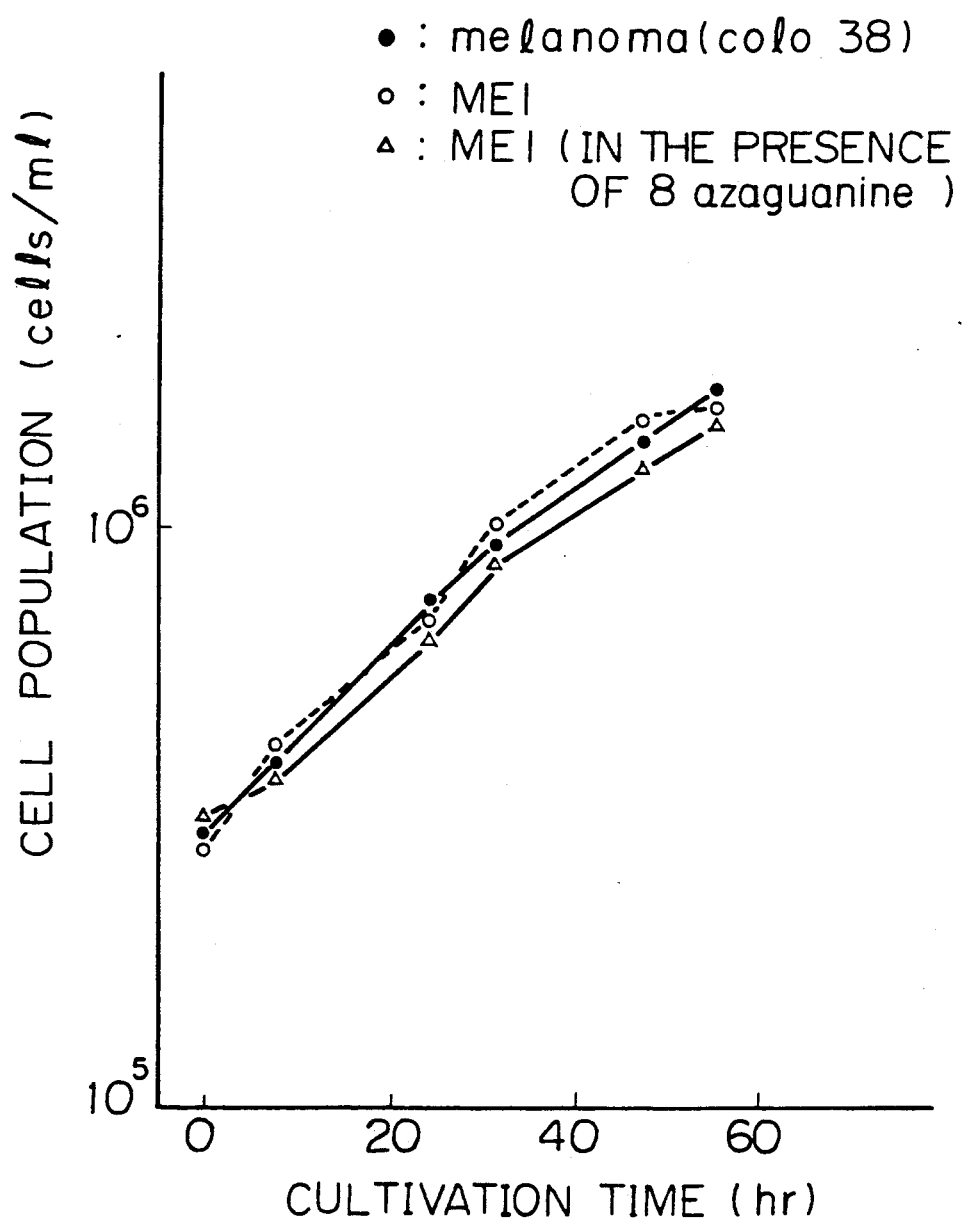
FIG. 3 is a graph depicting three growth curves, one for melanoma and the others for the parent cell line (ME 1) according to the present invention for hybridoma preparation.

The four clones of hybridoma prepared in Example 8 also had growth profiles similar to that of SUN N-21-1, although this is not shown in FIG. 3.

What is claimed is:

1. A process for producing a monoclonal antibody by cultivating a hybridoma which is prepared by fusion between mouse B cells immunized with an antigen and 8-azaguanine resistant cells of Colo 38 cell line.

2. A hybridoma between (i) a mouse B cell immunized with an antigen, and
(ii) an 8-azaguanine resistant Colo 38 cell, wherein said hybridoma is capable of secreting monoclonal antibody corresponding to said antigen.

3. A method of producing an antibody producing hybridoma by a fusing azaguanine resistant Colo 38 cells which are deficient in hypoxanthine-guanine phosphoribosyl transferase or with mouse B cells immunized with an antigen.

* * * * *